United States Patent [19]

Vogel

[11] Patent Number: 5,755,741
[45] Date of Patent: May 26, 1998

[54] BODY POSITION AND ACTIVITY SENSOR

[75] Inventor: Alan B. Vogel, Saugus, Calif.

[73] Assignee: Pacesetter, Inc., Sylmar, Calif.

[21] Appl. No.: 678,622

[22] Filed: Jul. 10, 1996

[51] Int. Cl.$^6$ .................................... A61N 1/362
[52] U.S. Cl. .................................................. 607/19
[58] Field of Search ........................ 607/19; 128/782; 340/686, 689, 429, 440; 200/224, 225, 229, 220

[56] References Cited

U.S. PATENT DOCUMENTS

| | | | |
|---|---|---|---|
| 3,701,093 | 10/1972 | Pick | 340/440 |
| 3,743,802 | 7/1973 | Avenick | 200/220 |
| 4,434,337 | 2/1984 | Becker | 200/229 |
| 4,811,491 | 3/1989 | Phillips et al. | 340/689 |
| 4,937,518 | 6/1990 | Donati et al. | 324/716 |
| 5,010,893 | 4/1991 | Sholder | 340/689 |
| 5,233,984 | 8/1993 | Thompson | 128/787 |

OTHER PUBLICATIONS

Evener et al. "Electrolytic Transducers as Monitoring Devices for Lateral Earth Movements in Civil Engineering Works" Electrolytic Transducers Monitoring Devices 1979.

Primary Examiner—William E. Kamm
Assistant Examiner—George R. Evanisko

[57] ABSTRACT

A sensor that is implantable within the body of a patient that provides an indication of movement and orientation of the patient. The sensor is comprised of a cylindrical enclosure having a central electrode positioned within the cavity formed by the enclosure that is co-axial with the axis of the cylinder. One or more peripheral electrodes are positioned within the cavity and extend in a direction parallel to the central electrode. An electrolytic fluid is positioned in the enclosure so that movement of the sensor results in variations in the amount of electrolytic solution between the central electrode and the one or more peripheral electrodes. An alternating current signal is applied to the central electrode and the one or more peripheral electrodes and the resulting voltage signal is measured between the central electrode and the one or more peripheral electrodes. The voltage signal will vary depending upon the amount of solution located between the central electrode and the peripheral electrodes thereby giving an indication of the orientation of the sensor. The leads for the electrodes preferably extend out of a single surface in a single direction to permit mounting on a planar mounting plate. Further, the peripheral electrodes are preferably configured so that each point on an inner surface of the peripheral electrodes is substantially the same distance from the central electrode to prevent localized corrosion or build-up of electrostatic plating.

20 Claims, 3 Drawing Sheets

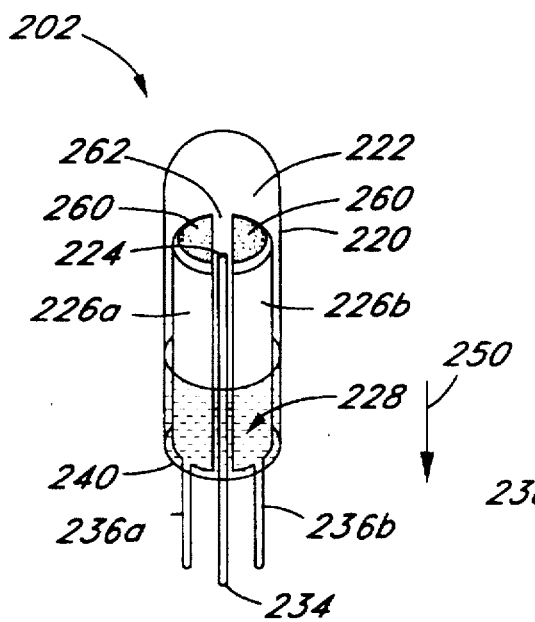
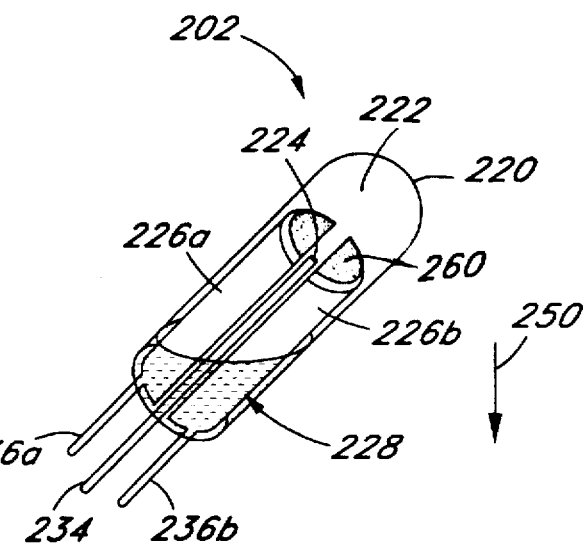
Fig. 2A   Fig. 2B
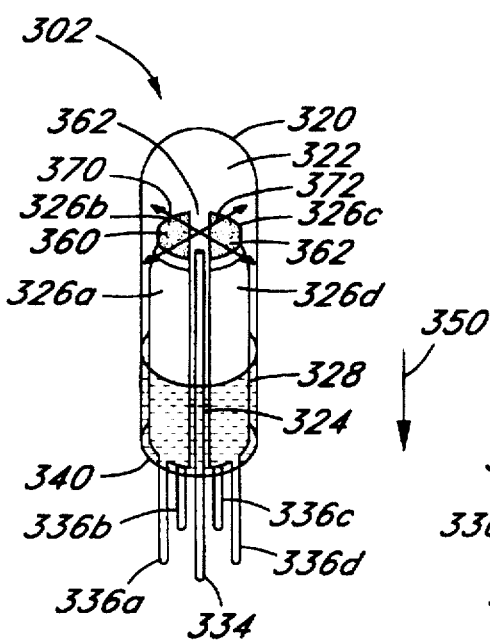
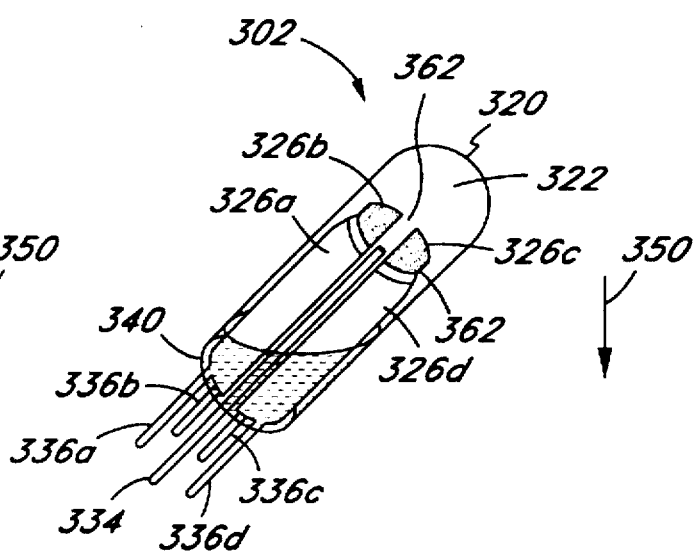
Fig. 3A   Fig. 3B

BODY POSITION AND ACTIVITY SENSOR

FIELD OF THE INVENTION

The present invention generally relates to a device for sensing body position and activity of a patient and, in particular, relates to a sensor which can be positioned within the body of the patient and can send signals to a control unit of an implantable electrical device indicative of the orientation and activity of the patient.

BACKGROUND OF THE INVENTION

Implantable electrical devices are commonly used for therapeutic purposes. These types of devices include cardiac pacemakers which provide therapeutic shocks to the heart of a patient to ensure proper heart function. These types of devices have become increasingly sophisticated as electronic circuitry has become more capable. For example, the pacemakers that are available today can sense the function of the heart and only provide therapeutic shocks upon detecting that the heart is experiencing some form of arrythmia.

It is understood that the organs in a patient's body perform differently in different circumstances. For example, the heart slows down its pulse rate when a person is sleeping and the heart increases its pulse rate when the person is active. With the increasing sophistication of pacemakers, it is desirable to be able to sense the activity of the patient and modify the function of the pacemaker accordingly. However, it is often difficult to accurately sense the orientation and activity of the person.

One type of sensor used to determine the orientation of an object is a mercury switch. The mercury switch, in its simplest form, is comprised of two electrodes that are positioned within an enclosure. The enclosure also has mercury that forms a conductive path between the two electrodes when the switch is in a particular orientation. When the switch is not in this orientation, there is no conductive path between the electrodes. While mercury switches may be used for sensing orientations of an object, they are generally not readily adaptable for use in the body of a patient. Specifically, mercury is highly toxic and damage to the sensor can result in a release of mercury into the body of the patient. Further, mercury switches are generally limited in the amount of information that they can convey in that they provide an indication as to whether or not the sensor is in a particular orientation. Consequently, the data provided by a mercury switch is often digital in nature as opposed to analog in nature.

Other types of position and orientation sensors have been developed in the prior art. One such sensor is disclosed in U.S. Pat. No. 5,233,984 to Thompson. Thompson discloses a sensor that is comprised of a generally cubical enclosure that has a central electrode positioned therein with side electrodes mounted on each of the walls of the cube. The relative resistance between the central electrode and any of the two side electrodes can be determined which provides an indication as to the orientation of the sensor.

One difficulty that the sensor disclosed in U.S. Pat. No. 5,233,984 has is that the enclosure is rectangular in configuration and the fluid will not flow evenly in the sensor when the sensor changes orientations. This results in discontinuities wherein the resistance signal changes abruptly. These discontinuities in the resistance signal sensed by the sensor can result in erroneous data. Further, since each of the side sensors are mounted on each of the walls of the enclosure, the leads for the sensor emanate in six different directions from the sensor. This makes mounting of this sensor difficult and it requires additional space. It will be appreciated that, in applications such as pacemakers, space is at a premium.

Yet a further difficulty with the sensor disclosed in U.S. Pat. No. 5,233,984 is that it appears the sensor will experience problems as a result of localized electrolytic plating. Specifically, since different electrical potentials are placed on the side electrodes and the central electrode, ions from one of these electrodes will travel to another. It is a well-known electrolytic phenomenon that the ions travel through the electrolytic solution along the shortest path. Hence, the portions of the side electrodes closest to the central electrode are likely to be depleted, or coated, at a greater rate than the portions of the electrodes towards the outer edges of the side electrodes. This can result in either the side electrodes eventually shorting across to the central electrode or in portions of the side electrodes being completely corroded away in an area adjacent the central electrode. Hence, the sensor disclosed in U.S. Pat. No. 5,233,984 is more likely to periodically fail. It will be understood that in applications such as implanted pacemakers, longevity of the component parts is desired as replacement is difficult and invasive to the patient.

Hence, there is a need in the prior art for a sensor that is capable of providing a signal representative of the orientation of the sensor that can be used in conjunction with implanted electrical devices. To this end, there is a need for a sensor which is compact in configuration, easily mounted to an implanted electrical device, has an increased useful life and provides accurate data indicative of the orientation of the sensor.

SUMMARY OF THE INVENTION

The aforementioned needs are satisfied by the sensor of the present invention which is comprised of a cylindrical enclosure which has an electrolyte solution contained therein. The enclosure also includes a central electrode and a plurality of side electrodes wherein the plurality of side electrodes preferably have a radius of curvature so that a uniform distance is maintained between the central electrode and the inner surface of the side electrodes. The sensor is also equipped with a driving circuit which provides a current signal to the electrodes so that the relative voltage between the central electrode and two of the side electrodes can be measured. Preferably, the current signal that is applied is an alternating voltage to limit electrolytic plating on the electrode. The resistance between the central electrode and two side electrodes mounted on opposite sides of the central electrode varies depending upon the quantity of the electrolyte solution that is positioned between the central electrode and the side electrodes. Hence, the position sensor produces varying resistance signals between the central electrode and the side electrodes that are indicative of the orientation of the sensor.

In one aspect of the present invention, each of the electrodes has a lead which extends out of a first surface of the cylindrical enclosure. It will be appreciated that this facilitates mounting of the sensor on a mounting plate in that a single uniform footprint can be configured to receive the pins of the sensor. In one embodiment of the preferred invention, the sensor is comprised of two side electrodes and a central electrode which provide a signal that is indicative of motion in a single direction. In another embodiment of the present invention, a sensor is provided which has a central electrode and four side electrodes positioned on four opposing sides of the central electrode. It will be appreciated that this sensor provides signals indicative of motion in two directions.

In another aspect of the present invention, the enclosure containing the electrodes has one or more wells that receive substantially all of the electrolyte solution when the sensor is in a particular configuration. Specifically, the enclosure in one preferred embodiment is mounted in the patient so that, when a patient is lying down, the electrolyte solution within the enclosure drains out of a region that contains the central electrode and one or more side electrodes and into a well so that a sensory circuit which detects the resistance between the central electrodes and the side electrodes sees a significantly higher resistance. This sensor is suitable for providing a signal indicative of when the patient is lying down which can be used by a pacemaker controller to moderate the pacing pulses provided to the heart to a rate which is consistent with the patient sleeping.

Hence, the sensor of the present invention provides an accurate indication as to the orientation of the sensor and can therefore be used to provide an indication to a pacemaker controller indicative of the orientation of a patient wearing the sensor. It will be further appreciated that activity by the sensor will result in movement of the solution within the sensor which can be detected by the detection circuit. High activity of the solution can then be interpreted by the sensor as increased activity by the patient which can then be used by the pacemaker controller as an indication of the need to increase the pacing rate of the pacemaker controlling the heart.

It will be further appreciated that the sensor of the present invention is configured to have an increased longevity. Specifically, in one aspect, the sensor has a driving circuit which provides an alternating voltage source and also has side electrodes that are curved so as to maintain a substantially uniform distance between the side electrodes and the central electrodes. It will be appreciated that this configuration of the electrodes significantly reduces the problem of localized regions of the side electrodes being fully consumed by corrosion or fully coated by plating.

These and other objects and advantages of the present invention will become more fully apparent from the following description taken in conjunction with the accompanying drawings.

BRIEF DESCRIPTION OF THE DRAWINGS

FIGS. 2A and 2B are perspective views of one embodiment of a body position sensor used in the circuit of FIG. 1;

FIGS. 3A and 3B are perspective views of another embodiment of the body position sensor used in the circuit of FIG. 1.

DETAILED DESCRIPTION OF THE PREFERRED EMBODIMENTS

Figure 1:
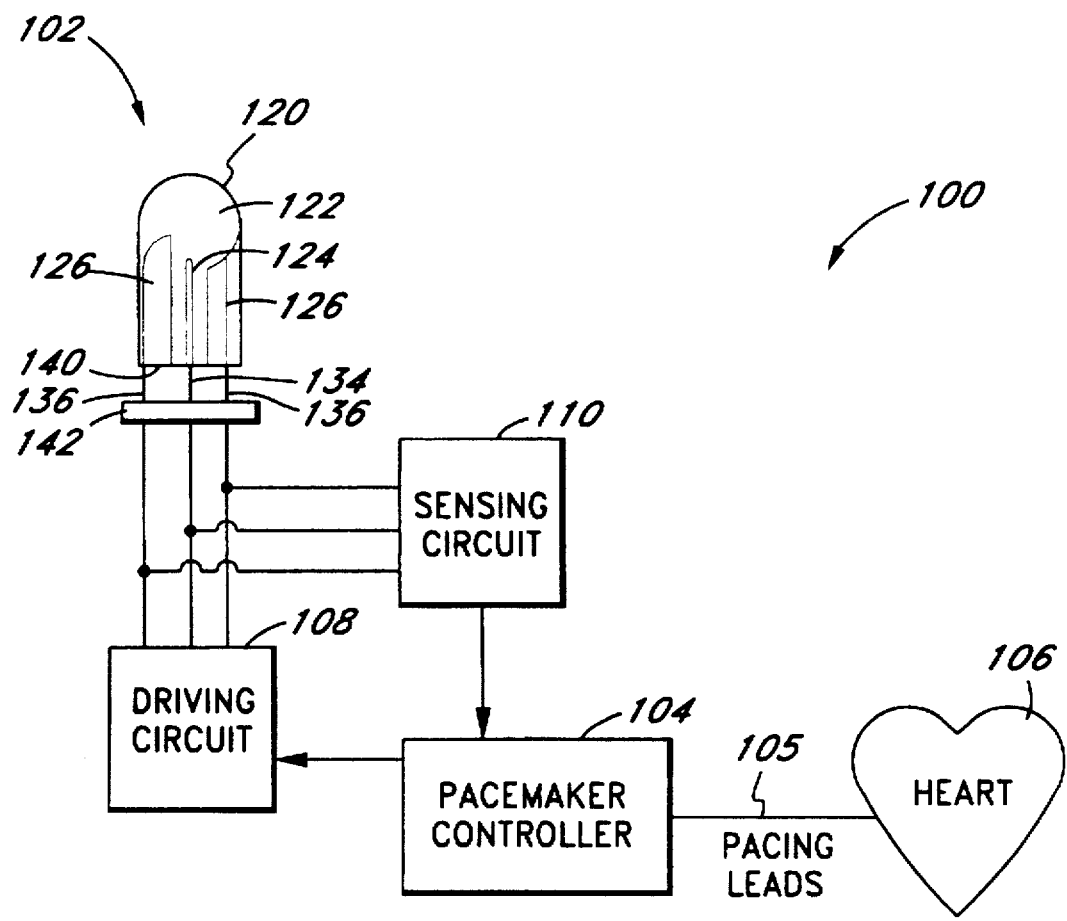
FIG. 1 is a schematic view of a pacemaker system that incorporates one of the preferred embodiments of a body position sensor.

Reference will now be made to the drawings wherein like numerals refer to like parts throughout. FIG. 1 is a schematic that illustrates a pacemaker controlling circuit 100 that incorporates a body position sensor 102 of the present invention. Preferably, the circuit 100 includes a pacemaker controller 104 that provides pacing signals via one or more implanted pacing leads 105 to a heart 106. The pacemaker controller and the pacing leads 105 are typical of any of a number of implantable pacemaker controllers and pacing leads used in the prior art.

The circuit 100 includes a driving circuit 108 that provides voltage signals to electrodes mounted within the sensor 102. Specifically, the sensor 102 includes a generally cylindrical enclosure 120 that defines a cavity 122 wherein a central electrode 124 is positioned, preferably coaxially with the center axis of the cylindrical enclosure 120, and a plurality of side electrodes 126 are mounted towards the inner wall of the enclosure 120 on opposing sides of the central electrode 124. As is discussed in greater detail hereinbelow, the cavity 122 includes an electrically conductive electrolyte which partially fills the cavity 122. Variations in the orientation of the sensor 102 about an axis defined by the central electrode 124 results in variations in the quantity of conductive electrolyte that is positioned between the central electrode 124 and the side electrodes 126. The central electrode 124 has a lead 134 which extends through a first surface 140 of the enclosure 120 and is mounted in a mounting plate 142. Similarly, the plurality of side electrodes 126 have a plurality of leads 136 connected thereto that extend through the first surface 140 and are mounted in the mounting plate 142. In the preferred embodiment, the mounting plate 142 is comprised of a printed circuit board that has a footprint of pin receptors (not shown) that is configured to receive the leads 134 and 136 and defines a plane that receives the leads 134 and 136. Hence, it will be appreciated that the body position sensor 102 simply has to be mounted on the mounting plate 142 in the same manner that electronic components are typically mounted on printed circuit boards to connect the body position sensor 102 to the rest of the pacemaker circuit 100.

Specifically, the driving circuit 108 is electrically connected to the footprint of pin receptors on the mounting plate 142 so as to be electrically connected to each of the leads 134, 136. Similarly, a sensing circuit 110 is also electrically connected to the pin receptors on the mounting plate 142 so as to be electrically connected to the leads 134 and 136. In the preferred embodiment, the driving circuit provides an alternating current signal to the central electrode 124 and the plurality of peripheral electrodes 126 and the sensing circuit 110 senses the resulting voltage signal between the central electrode 124 and the plurality of peripheral electrodes 126.

It will be appreciated that the voltage signal sensed by the sensing circuit 110 between the central electrode 124 and any one of the plurality of peripheral electrodes 126 is dependent upon the quantity of electrolyte material that is positioned between the central electrode 124 and the plurality of peripheral electrodes 126. Further, the quantity of electrolyte that is positioned between the central electrode 124 and the plurality of peripheral electrodes 126 is dependent upon the orientation of the body position sensor 102 about the axis defined by the central electrode 124. Hence, movement of the patient about this axis will vary the amount of electrolyte material between the central electrode 124 and the peripheral electrodes 126 which is sensed by the sensing circuit 110.

The sensing circuit 110 therefore provides a signal to the pacemaker controller 104 that is indicative of the orientation and movement of the patient. This information can be used by the pacemaker controller 104 to vary the pacing signals being provided to the heart 106 via the pacing leads 105. For example, it may be desirable to slow down the frequency of pacing pulses being provided to the heart 106 in response to detecting that the patient is lying down and is possibly asleep. Further, if the voltage signal remains relatively constant, then the pacemaker controller 104 can conclude that the patient is relatively motionless and can slow down the patient's heart rate accordingly.

Alternatively, it may be desirable to increase the frequency of pacing pulses being provided to the patient upon the sensing circuit 110 detecting fluctuations in the sensed voltage between the central electrode 124 and the plurality of peripheral electrodes 126 which indicates that the patient is engaging in physical activity. Specifically, it will be appreciated that sudden movements of the patient containing the sensor will result in sudden variations of the amount of electrolyte fluid between the central electrode 124 and the side electrodes 126. These will generally appear to the sensing circuit 110 as high frequency variations in the signal provided by the sensor 102. The presence of these high frequency variations can then be transmitted to the pacemaker controller 104 as being indicative of sudden motions and high activity of the patient thereby requiring a faster pacing rate.

It will be understood from the following description that one of several possible configurations of body position sensors 102 can be used in the pacemaker circuit 100 of the preferred embodiment. These different configurations of body position sensors will now be described in greater detail in reference to FIGS. 2–4.

FIGS. 2A and 2B illustrate one embodiment of a body position sensor 202 in two different orientations. The body position sensor 202 includes a generally cylindrical enclosure 220 that defines a cylindrical cavity 222. A central electrode 224 is positioned so as to be coaxial with the central axis of the cylindrical cavity 222. Two peripheral electrodes 226a and 226b are positioned adjacent the inner walls of the enclosure 220. A central electrode lead 234 and two peripheral electrode leads 236a and 236b are connected to the central electrode 224 and the peripheral electrodes 226a and 226b, respectively, and extend out of a first surface 240 of the enclosure 220. As shown in FIG. 2A, a conducting electrolyte solution 228 is positioned within the cavity 222 so as to partially fill the cavity 222. The electrolyte solution 228 is preferably a biocompatible electrolyte that has sufficiently low surface tension characteristics so that changes in the orientation of the sensor will result in the electrolyte solution uniformly flowing with respect to gravity.

In particular, FIG. 2A illustrates a sensor 202 in a first position wherein the central electrode 224 is positioned so as to be parallel to the direction of gravitational attraction as represented by arrow 250. In this position, a substantially equal amount of electrolyte solution 228 is positioned between the central electrode 224 and both of the peripheral electrodes 226a and 226b. However, as shown in FIG. 2B, when the sensor 202 is moved so that the central electrode 224 is no longer parallel to the direction of gravitational attraction as represented by arrow 250, the amount of electrolyte solution 228 between the central electrode 224 and one of the peripheral electrodes 226b is increased whereas the amount of electrolyte solution between the central electrode 224 and the other peripheral electrode 226a is decreased. Consequently, the sensing circuit 110 (FIG. 1) senses a decrease in the resulting voltage between the central electrode 224 and the peripheral electrode 226b and an increase in the resulting voltage between the central electrode 224 and the peripheral electrode 226a. This change in voltage is the result of more electrolyte solution 228 being positioned between the central electrode 224 and the peripheral electrode 226b which forms a lower resistance path for conductors between these two electrodes. Similarly, the decrease in the electrolyte solution 228 between the central electrode 224 and the other peripheral electrode 226a results in a higher resistance path between these two electrodes.

The sensing circuit 110 can then provide this information to the pacemaker controller 104 which provides the pacemaker controller with an indication as to the orientation of the patient.

The peripheral electrodes 226a and 226b are preferably comprised of two half cylinders of a conductive material such as gold or aluminum that are oriented about the central electrode 224 so that each point on an inner surface 260 of the electrodes 226a and 226b is a substantially equal distance from the central electrode 224. Preferably, the central electrode 224 is cylindrical in shape so that the uniformity of distance between the inner surfaces 260 of the peripheral electrodes 226a and 226b is substantially maintained. It will be appreciated that since the inner surfaces 260 and 224 are curved in this fashion, that corrosion and/or build-up of deposits on a particular point of the peripheral electrodes 226a and 226b and the central electrode 224 is reduced.

The body position sensor 202 shown in FIGS. 2A and 2B is capable of providing a signal that is indicative of the orientation of the sensor in a plane that is parallel to the center electrode and perpendicular to the plane of the inner surfaces 260 of the peripheral electrodes 226a and 226b. There are two gaps 262 between the two peripheral electrodes 226a and 226b that maintain electrical isolation between the two peripheral electrodes. The sensitivity of the body position sensor 202 is reduced as the plane of motion of the sensor is parallel to the plane defined by the gaps 262. Conversely, the body position sensor 202 is most sensitive to motion that is directly perpendicular to a plane defined by the two gaps 262 between the peripheral electrodes 226a and 226b. It will be appreciated that it may be desirable to have increased sensitivity to motion in two different directions. In other words, it may be desirable to provide the controller 104 with a first signal that is indicative of motion in a first direction and a second signal that is indicative of motion in a second direction. To address this problem, another embodiment of a sensor 302 shown in FIGS. 3A and 3B can be used.

Specifically, FIG. 3A shows that the sensor 302 includes an enclosure 320 that is generally cylindrical in shape and defines a cylindrical cavity 322. Positioned within the cavity 322 is a central electrode 324 which extends generally coaxially with the axis of the cavity 322. There are four peripheral electrodes 326a–326d that are equally spaced apart about the circumference of a circle centered about the central electrode 324 so as to be oriented in quadrants about the central electrode 324. Preferably, the peripheral electrodes 326a–326d are curved so that the inner surfaces 362 of each of the peripheral electrodes 326a–326d are spaced a uniform distance from the central electrode 324 for the reasons given above. Further, there is a lead 334 that is connected to the central electrode 324 and a lead 336a–336d that is connected to each of the peripheral electrodes 324a–324d, respectively, that extend out of the first surface 340 of the enclosure 320 in the manner described above. An electrolyte solution 328 is positioned within the cavity 322.

As shown in FIG. 3A, the sensor 302 is substantially similar to the sensor 202 shown in FIGS. 2A and 2B except that there are four peripheral electrodes that can provide signals to the sensing circuit 110 in response to the driving circuit 108 applying a current. Hence, the sensing circuit 110 can receive a signal that is indicative of the change in resistance between the central electrode and the set of peripheral electrodes 326a and 326c and the central electrode and the set of peripheral electrodes 326b and 326d.

In other words, the sensor 302 provides signals which are indicative of motion in two orthogonal directions represented by the arrows 370 and 372. Specifically, motion that is orthogonal to the plane of the inner surfaces 362 of the peripheral electrodes 326a and 326c, will result in a change in the quantity of electrolyte solution 328 between the two peripheral electrodes 326a and 326c and the central electrode 324. Similarly, movement in the direction that is orthogonal to the inner surfaces 362 of the peripheral electrodes 326b and 326d will result in a change in the quantity of electrolyte solution 328 between these two peripheral electrodes 326b and 326d and the central electrode 324. Hence, the sensor 302 can be used in the circuit 100 (FIG. 1) so that the sensing circuit 110 is capable of providing the pacemaker controller 104 of two signals that are indicative of motion in two orthogonal directions. It will be further appreciated that increasing the number of peripheral electrodes spaced symmetrically about the central electrode will increase the directions of motion that can be sensed by the sensing circuit 110.

Figure 4A:
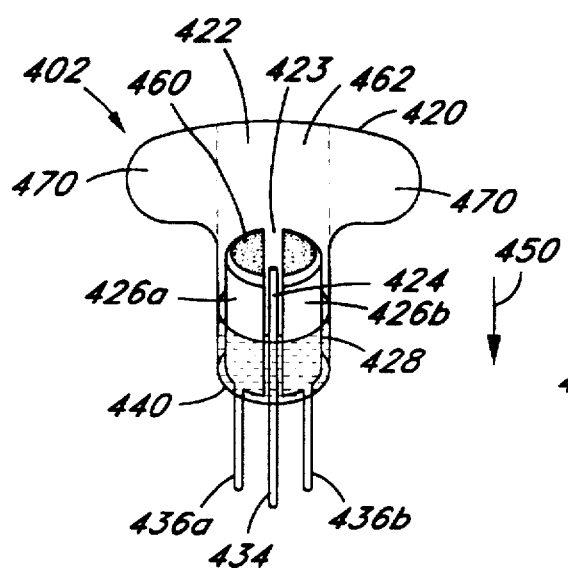
FIGS. 4A and 4B are perspective views of yet another embodiment of a body position sensor used in the circuit of FIG. 1.
Figure 4B:
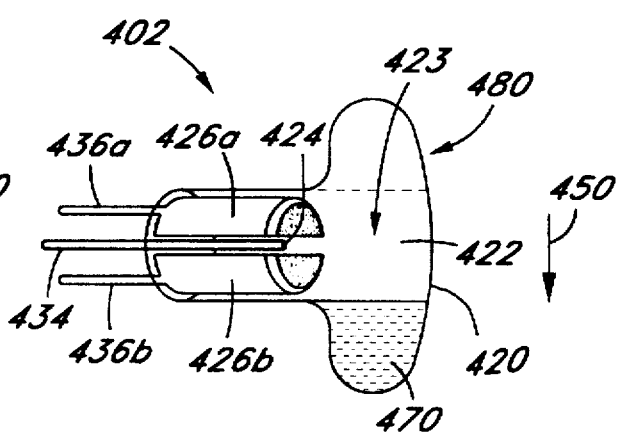

FIGS. 4A and 4B illustrate yet another embodiment of a body position sensor 402 that can be used in the pacemaker circuit 100 (FIG. 1). Specifically, the sensor 402 is configured so that when the sensor is in a first orientation, the sensor 402 provides a clear signal that it is in the first orientation. It will be appreciated that, in some applications, it may be desirable to send a signal to the pacemaker controller 104 that the patient is in a first orientation, e.g., substantially horizontal such as when sleeping, that will be unaffected by subsequent motion of the patient that does not remove the patient from the first orientation. The sensor 402 includes an enclosure 420 that defines a cavity 422 having a cylindrical portion 423 and a well 470 which extends radially outward from the cylindrical portion 423 of the cavity 422. Mounted within the cavity 422 is a central electrode 424 and two or more peripheral electrodes 426 that are similar in construction to the central electrodes and peripheral electrodes described hereinabove. Leads 434 and 436a and 436b are attached to the central electrode 424 and the peripheral electrodes 426 respectively in the manner described above. The electrolyte solution 428 is positioned within the cavity 422 so that movement of the sensor 402 results in differential changes in the amount of electrolyte solution between the central electrode 424 and the plurality of peripheral electrodes 426 in the manner described above. Hence, for small changes in orientation, the operation of the sensor 402 is substantially similar to the operation of the sensors 202 and 302 described hereinabove.

A unique aspect of the sensor 402 is the well 470 that is formed in the enclosure 420. Generally, the well 470 is comprised of an annular ring-shaped well that extends around the outer circumference of the enclosure 420. As shown in FIG. 4B, when the sensor 402 is oriented so that the central electrode 424 extends in a direction that is substantially perpendicular to the direction of gravity 450, the electrolyte solution 428 flows into the well 470. Hence, the sensing circuit 110 (FIG. 1) would sense an infinite resistance between the central electrode 424 and the peripheral electrodes 426 as there is no electrolyte solution 428 positioned between the central electrode 424 and the peripheral electrodes 426 when the sensor is in this orientation. It will be appreciated that this will provide a clear signal to the pacemaker controller 104 that the sensor is in this first orientation.

It will be further appreciated that if the sensor 402 is oriented in the body of the patient so that it enters the first orientation upon the patient lying down, that the sensor 402 provides a clear signal to the pacemaker controller 104 that the patient is lying down. Further, the sensor 402 is less sensitive to motions of the patient while the patient is in the first orientation as a result of the electrolyte solution 428 being positioned in the well 470. For example, if the sensor 402 is positioned within the patient so that it enters the first orientation when the patient is lying down, as the patient rolls over or moves during their sleep, the voltage measurements of the sensing circuit 110 will largely be unaffected by this motion as most of the electrolyte solution 428 will remain within the well 470. Consequently, the sensor 402 is particularly adaptable to be mounted in patients to provide a signal that indicates that the patient is lying down or sleeping. The pacemaker controller 104 (FIG. 1) can then use the signal to adjust the pacing rate of the heart to accommodate for less physical activity.

From the foregoing it will be appreciated that the particular embodiment of the sensor used in each implementation will vary depending upon the sensing needs of the pacemaker controller for each patient. However, the sensors of the preferred embodiments provide ease in mounting in that each of the leads of the sensors extend out of a first surface of the sensor which allows the sensor to be mounted on a planar mounting block that has a footprint of pin receptors that are configured to receive the leads. Further, the embodiments of the sensors described hereinabove are also less likely to experience spot degradation of the electrodes as the electrodes are configured to be a substantially uniform distance from a central electrode. Finally, from the foregoing it will be appreciated that the configuration of the enclosure that contains the electrodes can be configured so that particular orientations of the sensor will produce a first signal that is relatively insensitive to subsequent motions of the sensor while the sensor remains in the first orientation.

Although the foregoing description of the preferred embodiment of the present invention has shown, described, and pointed out the fundamental novel features of the invention, it will be understood that various omissions, substitutions, and changes in the form of the detail of the apparatus as illustrated, as well as the uses thereof, may be made by those skilled in the art without departing from the spirit of the present invention. Consequently, the scope of the invention should not be limited to the foregoing discussion, but should be defined by the appended claims.

What is claimed is:

1. A sensor that is implantable within a body of a patient and provides at least one signal that is indicative of the orientation of the sensor, the sensor comprising:

cylindrical enclosure having a first end and extending along an axis from the first end wherein said cylindrical enclosure defines a generally cylindrical cavity and has a first surface at a first end wherein said cylindrical enclosure is configured so that said cylindrical enclosure is adapted for implantation in the body of the patient so that said cylindrical enclosure is in a fixed orientation so that movement of the body results in corresponding movement of the enclosure;

a central electrode positioned within the cavity and mounted on the first surface so as to extend substantially parallel to the axis of the cylindrical cavity;

a plurality of peripheral electrodes positioned within the cavity about the central electrode so as to extend from the first surface in a direction substantially parallel to the axis of the cylindrical cavity wherein the plurality of peripheral electrodes are comprised of electrodes that are planar in configuration with an inner surface that is curved so that each point on the inner surface is substantially the same distance from the central electrode;

an electrolytic solution positioned in the cavity wherein movement of the sensor about the axis of the cavity while the sensor is implanted in a fixed orientation with respect to the body so that movement of the body results in corresponding movement of the sensor results in variations in the quantity of electrolytic solution positioned between the central electrode and the plurality of peripheral electrodes; and a circuit, that is connected to the central electrodes and the plurality of peripheral electrodes, that applies an electrical signal between the central electrodes and at least one of the peripheral electrodes so that when the electrical signal is applied between the central electrode and at least one of the peripheral electrodes, the circuit obtains a signal between the central electrode and at least one of the plurality of peripheral electrodes which is indicative of the movement of the sensor and is thereby indicative of movement of the body when the sensor is implanted in the body of the patient in a fixed orientation with respect to the body.

2. The sensor of claim 1, wherein the plurality of peripheral electrodes is comprised of two electrodes that are positioned on opposite sides of the central electrode and wherein the circuit obtains a signal indicative of the orientation of the sensor in a plane that is parallel to the center electrode and perpendicular to the plane of the inner surfaces of the two peripheral electrodes.

3. The sensor of claim 1, wherein the plurality of peripheral electrodes is comprised of four electrodes that are circumferentially positioned about the central electrode in four quadrants and wherein the circuit obtains a first signal indicative of motion of the sensor in a first direction that is perpendicular to the plane of the inner surface of a first two peripheral electrodes positioned on opposite sides of the central electrode and wherein the circuit obtains a second signal indicative of motion of the sensor in a second direction that is perpendicular to the plane of the inner surface of a second two peripheral electrodes positioned on opposite sides of the central electrode.

4. The sensor of claim 1, further comprising a central electrode lead that is connected to the central electrode and a plurality of peripheral electrode leads that are connected to the plurality of peripheral electrodes wherein the central electrode lead and the plurality of peripheral electrodes leads extend out of a bottom surface of the first surface of the enclosure in a substantially parallel direction and can therefore be mounted on a plurality of pin receptors positioned in a single plane.

5. The sensor of claim 1, wherein the enclosure also defines a well that is configured so that substantially all of the electrolytic solution enters the well when the sensor is in a first orientation so that the electrical circuit obtains a first signal indicating that the sensor is in the first orientation in response to the circuit applying the electrical signal between the central electrode and the plurality of peripheral electrodes.

6. The sensor of claim 5, wherein the well is configured so that subsequent motion of the sensor, while the sensor remains in the first orientation, does not produce a change in the first signal produced by the sensor.

7. The sensor of claim 6, wherein the sensor is configured to be mounted in the body of a patient in the fixed orientation with respect to the body of the patient so that when the patient is lying down, the sensor is in the first orientation and the electrolytic solution is substantially positioned within the well and the well is further configured so that motion of the patient while the patient is lying down does not result in the electrolytic solution being dislodged from the well.

8. The sensor of claim 1, wherein the circuit comprises:

driving circuit that is connected to at least one of the central electrodes or the plurality of peripheral electrodes and provides a current signal thereto; and a sensing circuit that is connected to the central electrodes and the plurality of peripheral electrodes that measures voltage signals between the central electrode and the plurality of peripheral electrodes produced as a result of the current signal being provided to the electrodes wherein the voltage signals change as a result of the change in the quantity of the electrolytic solution positioned between the central electrode and any one of the plurality peripheral electrodes.

9. The sensor of claim 8, wherein when the sensor is mounted within the body of a patient in a starting orientation that is fixed with respect to the body of the patient, the sensing circuit is configured to provide a signal indicative of the change of orientation of the sensor as a result of motion of the patient.

10. The sensor of claim 9, wherein the sensing circuit is configured to provide a pacemaker controller with a signal indicative of the patient lying down and wherein the sensing circuit is also configured to provide signals indicative of heightened physical activity of the patient.

11. A pacing system that is implantable within the body of a patient and provides one or more signals that are indicative of movement of the patient, the system comprising:

a sensor adapted for implantation in the body of a patient in a fixed orientation with respect to the body so that movement of the body results in corresponding movement of the sensor that includes an enclosure having a first surface with a central electrode extending in a first direction into a cavity defined by the enclosure and at least two peripheral electrodes that extend from the first surface in the first direction in the cavity wherein the at least two peripheral electrodes are planar in configuration with an inner surface that is curved so that each point on the inner surface is substantially the same distance from the central electrode, and wherein the central electrode and the at least two peripheral electrodes are mounted on the first surface within the enclosure;

an electrolytic solution positioned within the enclosure wherein movement of the electrolytic solution results in variations in the quantity of electrolytic solution positioned between the central electrode and the at least two peripheral electrodes;

a central electrode lead that is connected to the central electrode and extends out of the first surface of the enclosure in a second direction;

at least two peripheral electrode leads that are connected to the at least two peripheral electrodes and extend out of the first surface of the enclosure in the second direction;

a mounting plate that defines a planar surface that receives the central electrode lead and the at least two peripheral electrode leads;

a driving circuit that provides an electrical signal to the central electrode;

a sensing circuit that senses an orientation signal in response to the driving circuit providing the electrical signal wherein the orientation signal is representative of the orientation of the sensor; and a pacemaker controller for controlling the delivery of pacing impulses delivered to a heart of the patient that receives the orientation signal from the sensing circuit and uses said orientation signal to adjust the delivery of pacing impulses to the heart of the patient.

12. The sensing system of claim 11, wherein the driving circuit provides an alternating current signal between the central electrode and the at least two peripheral electrodes wherein the alternating current signal alternates in polarity to reduce the occurrence of electroplating on either the central electrode or the at least two peripheral electrodes.

13. The sensing system of claim 11, wherein the sensing circuit provides a signal to the pacemaker controller that is indicative of heightened activity of the patient.

14. The sensing system of claim 13, wherein the sensing circuit provides a signal to the pacemaker controller that is indicative of decreased activity of the patient.

15. The sensor of claim 11, wherein the at least two peripheral electrodes are comprised of two electrodes that are positioned on opposite sides of the central electrode and provide a signal indicative of the orientation of the sensor in a plane that is parallel to the center electrode and perpendicular to the plane of the inner surfaces of the two electrodes.

16. The sensor of claim 15, wherein the at least two peripheral electrodes is comprised of four electrodes that are circumferentially positioned about the central electrode in four quadrants and provide a first signal indicative of motion of the sensor in a first direction that is perpendicular to the plane of the inner surface of a first two peripheral electrodes positioned on opposite sides of the central electrode and provide a second signal indicative of motion of the sensor in a second direction that is perpendicular to the plane of the inner surface of a second two peripheral electrodes positioned on opposite sides of the central electrode.

17. The sensor of claim 16, wherein the enclosure also defines a well that is configured so that substantially all of the electrolytic solution enters the well when the sensor is in a first orientation so as to produce a first signal indicating that the sensor is in the first orientation.

18. The sensor of claim 17, wherein the well is configured so that subsequent motion of the sensor, while the sensor remains in the first orientation, does not produce a change in the first signal produced by the sensor.

19. The sensor of claim 18, wherein the sensor is configured to be mounted in the body of a patient so that when the patient is lying down, the sensor is in the first orientation and the electrolytic solution is substantially positioned within the well and the well is further configured so that motion of the patient while the patient is lying down does not result in the electrolytic solution being dislodged from the well.

20. An implantable sensor for detecting body position and body movement, the sensor comprising:

an elongated central electrode having a terminal portion;

at least two side electrodes having a length, an inner surface and a radius of curvature so that a uniform distance is maintained between the central electrode and the inner surface of the side electrodes, each of the side electrode having at terminal portion;

a cylindrical enclosure defining a generally cylindrical cavity and having an open end, a sealed end and a central axis, the cylindrical enclosure being adapted for implantation in a patient;

mounting means, dimensioned to fit within the open end of cylindrical enclosure, for mounting the at least two side electrodes so as to be coaxial about the central electrode and extending in a direction substantially parallel to the central axis of the cylindrical enclosure, the mounting means including means for hermetically sealing the open end so that the terminal portions of each electrode extends to an exterior side of the mounting means; and an electrolytic solution positioned in the cavity such that when the sensor is implanted within a patient, movement of the sensor about the central axis of the cylindrical enclosure results in variations in the quantity of electrolytic solution positioned between the central electrode and the side electrodes so that when an electrical signal is applied to the central electrode, a signal is produced which is indicative of one of body position or body movement of the patient;

whereby the curvature of the side electrodes and the uniform distance to the central electrode minimizes corrosion and plating of the electrodes.

* * * * *